United States Patent
Konegger

(10) Patent No.: US 10,082,222 B2
(45) Date of Patent: Sep. 25, 2018

(54) DEVICE FOR QUICKLY VENTING AND DRAINING A FILTER

(71) Applicant: Fresenius Medical Care Deutschland GmbH, Bad Homburg (DE)

(72) Inventor: Mario Konegger, Innsbruck (AT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 501 days.

(21) Appl. No.: 14/649,320

(22) PCT Filed: Nov. 29, 2013

(86) PCT No.: PCT/EP2013/075103
§ 371 (c)(1),
(2) Date: Jun. 3, 2015

(87) PCT Pub. No.: WO2014/086681
PCT Pub. Date: Jun. 12, 2014

(65) Prior Publication Data
US 2015/0300524 A1   Oct. 22, 2015

Related U.S. Application Data

(60) Provisional application No. 61/732,628, filed on Dec. 3, 2012.

(30) Foreign Application Priority Data

Dec. 3, 2012  (DE) .................. 10 2012 023 504

(51) Int. Cl.
*F16K 31/18*   (2006.01)
*A61M 1/36*   (2006.01)
(Continued)

(52) U.S. Cl.
CPC .............. *F16K 31/18* (2013.01); *A61M 1/16* (2013.01); *A61M 1/1621* (2014.02);
(Continued)

(58) Field of Classification Search
CPC ........ F16K 31/18; F16K 31/20; F16K 24/042; F16K 24/046; B01D 61/30; B01D 36/001;
(Continued)

(56) References Cited

U.S. PATENT DOCUMENTS 3,424,184 A * 1/1969 Brimley ................ F16K 24/046
  137/102
3,900,230 A * 8/1975 Durling ................. B60T 11/326
  128/205.15
(Continued)

FOREIGN PATENT DOCUMENTS

DE  8603781  4/1986
DE  3444671  6/1986
(Continued)

*Primary Examiner* — Robert Clemente
(74) *Attorney, Agent, or Firm* — Jacobson Holman, PLLC.

(57) ABSTRACT

The invention discloses an air vent valve for venting a filter, having a cavity with an inlet and an outlet and a sealing element in the interior of the cavity for sealing the inlet in a first position and for sealing the outlet in a second position. The sealing element is freely movable between the first position and the second position, and a flow is created between the inlet and the outlet when the sealing element is in an intermediate position between the first position and the second position.

10 Claims, 3 Drawing Sheets

(51) Int. Cl.
| | |
|---|---|
| *B01D 63/02* | (2006.01) |
| *F16K 24/04* | (2006.01) |
| *A61M 1/16* | (2006.01) |
| *B01D 61/30* | (2006.01) |
| *F16K 31/20* | (2006.01) |
| *A61M 39/22* | (2006.01) |
| *B01D 36/00* | (2006.01) |
| *F16K 17/00* | (2006.01) |
| *A61M 39/24* | (2006.01) |

(52) U.S. Cl.
CPC ........ *A61M 1/3627* (2013.01); *A61M 1/3643* (2013.01); *A61M 1/3644* (2014.02); *A61M 39/22* (2013.01); *B01D 36/001* (2013.01); *B01D 61/30* (2013.01); *B01D 63/02* (2013.01); *F16K 17/00* (2013.01); *F16K 24/046* (2013.01); *F16K 31/20* (2013.01); *A61M 2039/2473* (2013.01); *A61M 2205/75* (2013.01); *B01D 2313/16* (2013.01); *B01D 2313/18* (2013.01)

(58) Field of Classification Search
CPC ............................ B01D 36/02; B01D 2313/16; B01D 2313/18; A61M 1/3627; A61M 1/16; A61M 1/1621; A61M 1/3643; A61M 39/22; A61M 2039/2473; A61M 2205/75

See application file for complete search history.

(56) References Cited

U.S. PATENT DOCUMENTS

| | | | | |
|---|---|---|---|---|
| 4,104,004 | A | * | 8/1978 | Graef ...................... F04B 53/06 137/202 |
| 4,320,001 | A | * | 3/1982 | Le Boeuf ............ A61M 1/3627 210/120 |
| 4,702,829 | A | | 10/1987 | Polaschegg et al. |
| 4,981,154 | A | * | 1/1991 | Bailey .................... F16K 15/04 137/199 |
| 2006/0091056 | A1 | * | 5/2006 | Brugger .............. A61M 1/3627 210/321.88 |
| 2011/0108482 | A1 | | 5/2011 | Lovell |

FOREIGN PATENT DOCUMENTS

| | | |
|---|---|---|
| DE | 4027531 | 7/1991 |
| DE | 102010025078 | 12/2011 |
| WO | WO 2006/049822 | 5/2006 |
| WO | WO 2011/058571 | 5/2011 |

\* cited by examiner

DEVICE FOR QUICKLY VENTING AND DRAINING A FILTER

The invention relates to an apparatus for venting a filter, preferably a hollow fiber filter in a dialysis liquid circulation.

Filters are used for cleaning gases and liquids in wide areas of the industry and in medicine. The filters that are used are designed so that they consist of two chambers separated from one another by a semipermeable membrane. The semipermeable membrane is such that liquid can be forced out of a first chamber, through the membrane and into a second chamber while higher-molecular substances are retained.

One area of application of fluid filters is in methods for fluid treatment or blood treatment such as hemodialysis or peritoneal dialysis.

In hemodialysis, blood in an extracorporeal circulation is taken from a patient continuously, passed through a hemodialyzer and reinfused back into the patient. This involves a mass exchange similar to that performed by the kidneys. The hemodialyzer consists of two chambers separated by a semipermeable membrane, with blood flowing through one chamber and a cleaning fluid—the dialysis fluid—flowing through the other. Commercial dialyzers usually have thousands of hollow fibers for this purpose, their walls forming the semipermeable membrane for the substances to be exchanged. Blood is passed through the interior of the hollow fibers while the dialysis fluid is usually fed into and removed from the hollow fiber interspace in the opposite direction.

The dialysis fluid has concentrations of blood ingredients such as electrolytes which correspond approximately to those in a healthy person, so that the corresponding blood concentrations can be kept at a normal level. Substances such as creatinine or urea that are to be removed from blood are not present in the dialysis fluid, so they are removed from the blood by diffusion based only on the concentration gradient on the membrane. Excess water is removed from the blood through convection and/or ultrafiltration with the help of a pressure gradient. The combined withdrawal achieved through convection and diffusion is referred to as diafiltration.

Hemodialysis machines which usually also ensure the preparation of the dialysis fluid of water and concentrates with the correct composition and temperature are used to control such processes. In hemodiafiltration, a larger quantity of ultrafiltrate is removed from the patient's blood by the hemodialyzer during a hemodialysis treatment and replaced by substitution fluid except for the total quantity of liquid to be removed, In modern machines for treatment of chronic renal failure, a dialysis fluid prepared online is used for this purpose by providing a line that branches off from the dialysis liquid circuit with one or more filter stages and by connecting it to the extracorporeal blood circulation upstream and/or downstream from the hemodialyzer. The addition of the extra-filtered dialysis fluid to the blood circulation is known as dilution.

At the start of the dialysis treatment, the filters arranged in the filter stages must be flushed with dialysis fluid and deaerated.

DE 4027531 C1 describes an arrangement which achieves venting by means of a hydrophobic filter at one upper end of a hollow fiber filter. One disadvantage of this arrangement is that the hydrophobic filter extends over the entire cross section of the hollow fiber filter and therefore does not have compressive stability. In addition, such a membrane is at a disadvantage with regard to manufacturing costs.

DE 3444671 A1 describes a method which achieves venting of a filter by means of a sterile filter and a hydrophobic filter. The filter to be vented is divided into two chambers having a connection for the supply of liquid at the lower end of the first chamber and a connection to an equalizing chamber and said hydrophobic filter at the upper end. The second chamber has a connection at the lower end, which is connected to said sterile filter and is arranged above said hydrophobic filter for venting. The venting is performed in such a way that liquid is introduced through the lower connection in the first chamber and the air in this chamber is displaced through the hydrophobic filter. As soon as all the air has been displaced, liquid is applied to the hydrophobic filter, which thus becomes impermeable for further passage of air. Then the liquid is forced through the membrane of the filter to be vented and it begins to displace the air in the second chamber through the sterile filter. As soon as essentially no more air is escaping through the sterile filter, the venting operation is concluded. One disadvantage of this method is that the sterile filter can be used only once.

Another disadvantage is that the hydrophobic filter is wetted with liquid and thus its sterility and compressive strength are no longer ensured.

If the sterility is impaired, there is an immediate risk that contaminants or microorganisms such as fungi and bacteria may be transferred from the substitution line into the patient's blood.

Another disadvantage is the need for repeated manual intervention on the part of the operating personnel.

WO 2006/049822 describes a method for venting a filter in which the filter is inclined slightly out of the vertical position. This achieves the result that air collects at the upper end of the filter at the highest location thereby formed. The venting can then be accomplished through this highest location, but one disadvantage here is a clamp that must be closed manually after venting.

It is known that hydrophobic filters allow gases or gas mixtures, in particular air and vapor to pass through but do not allow liquids and other solids, for example, bacteria and toxins to pass through. Because of this property, hydrophobic filters are used as sterile filters. If the membrane of the hydrophobic filter comes in contact with liquid, it also completely loses the property of gas and vapor permeability, so that it no longer has permeability. Furthermore, bacteria can settle on moist locations and can thereby reach the moist hydrophobic membrane.

In a dialysis fluid circulation with a hydrophobic filter and a connection closing it, the connection need not necessarily be sealed because the hydrophobic filter has compression resistance and normally has an elevated pressure in comparison with ambient pressure during the treatment. However, it is advantageous not to use the hydrophobic filter merely as a pressure barrier during treatment. This is a disadvantage in particular because pressure fluctuations caused by pumping in the dialysis fluid circulation, among other things, during the treatment may cause a variable compressive load on the hydrophobic filter membrane and increase the risk of breakage and thus unintentional escape of liquid and problems with dilution on the patient to be treated. In addition, a hydrophobic membrane may lose its effect as a sterile filter, so that there is an increased risk of contamination of the circulation on the blood side during the treatment.

SUMMARY

The object of the invention is therefore to overcome at least one of the aforementioned disadvantages and to provide a venting valve and a filter having a corresponding venting valve, which permits automatic venting.

This object is achieved with the venting valve according to the invention comprising a cavity (8) having a first opening (9) and a second opening (1) and a sealing element (7,29) in the interior of the cavity for sealing the first opening in a first position (4,28) and for sealing the second opening in a second position (3,24), wherein the sealing element is freely movable between the first position (4,28) and the second position (3,24), and wherein a flow is formed between the first and second openings (1) when the sealing element (7,29) is in an intermediate position between the first position (4,28) and the second position (3,24).

Advantageous refinements of the apparatus according to the invention are characterized below.

A venting valve for venting a filter, preferably a filter for a blood treatment machine, for example, a filter for a dialysis liquid circulation of a dialysis machine. The venting valve comprises a cavity having a first opening and a second opening and a sealing element in the interior of the cavity for sealing the first opening in a first position and for sealing the second opening in a second position. The sealing element is freely movable between the first and second positions, forming a flow passage between the first and second openings when the sealing element is in an intermediate position between the first and second positions.

In one embodiment, a vertical direction and a horizontal direction as well as an upper position and a lower position are predetermined during operation of the dialysis machine and thus during operation of the dialysis fluid circulation, and the sealing element is movable between the upper and lower positions during operation of the dialysis machine and the dialysis fluid circulation, such that the trajectory of movement between the upper and lower positions has a component in the vertical direction. In other words, the first position is a lower position and the second position is an upper position.

The sealing element is also advantageously designed as a float for floating on the dialysis fluid. In this way, a buoyant force with a vertical component, i.e., an upwardly directed component, contributes toward the sealing of the sealing element in the upper position.

In one embodiment, the surface of the sealing element comprises a hydrophobic material. However, the entire sealing element may also be made of hydrophobic material.

In the application in conjunction with a blood treatment and/or a blood treatment machine, one advantage of the apparatus disclosed herein is that the handling and the error tolerance in operation are improved and/or the necessary steps to be performed manually by the operating personnel are reduced. In addition, the cost of production is reduced.

DETAILED DESCRIPTION OF THE DRAWINGS

The apparatus according to the inventive teaching and advantageous refinements will be described in greater detail below with reference to FIGS. 1*a*, 1*b* and 1*c*, although the inventive teaching is not limited to this.

Figure 1A:
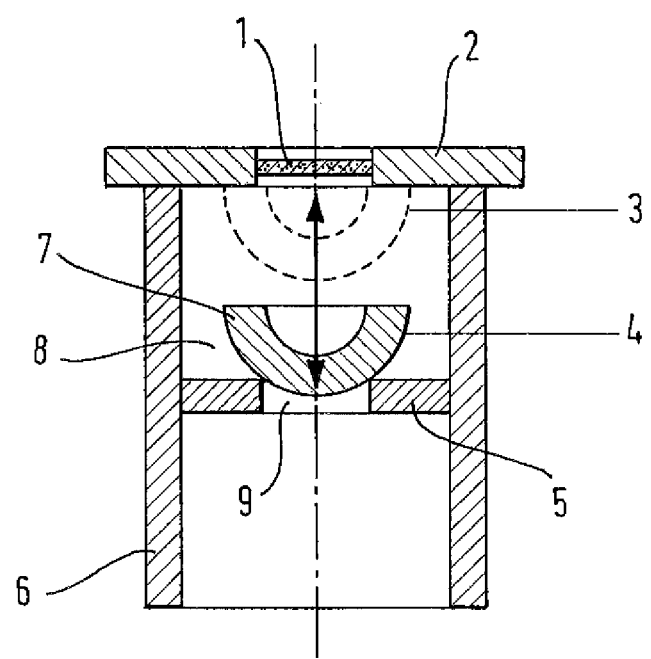
FIG. 1*a* shows a venting valve according to the teaching of the present invention.

FIG. 1*a* shows a venting valve for a dialysis liquid circuit of a dialysis machine having a hydrophobic membrane 1, which advantageously acts as a sterile filter at the same time, having a closing element 2, which is advantageously designed as a holding apparatus 2 for holding the hydrophobic membrane 1. Closing element 2 is connected to the body 6, which is preferably shaped to be cylindrical on the inside and is open in both directions, forming a tubular cavity and closing it completely at a first end. At a second end, the cylindrical interior of the body 6 is connected by means of the closing element 5 to an opening 9, which is preferably designed as a disk-shaped body with a hole arranged to run centrally and axially. The closing element 5 seals the interior of the body 6 at the bottom. In another embodiment, the body 6 may also shape the closing element 5. A movably arranged sealing element 7, which is shaped so that it forms an airtight, vapor-tight and/or fluid-tight connection by pressing against the closing element 2, is provided in the resulting cavity 8 in the interior of the body 6, such that the sealing element 7 can seal only one or one of the two closing elements, but not both at the same time. During operation of the dialysis machine, a horizontal orientation and a vertical orientation are defined, and an upper position 3 of the sealing element 7 and a lower position 4 of the sealing element 7 are defined. During operation of the dialysis, machine the sealing element 7 is movable between the lower position 4 and the upper position 3. The trajectory of movement between the lower position 4 and the upper position 3 thus contains at least one component in the vertical direction. Guide means (not shown) may be provided to ensure movement of the sealing element 7 along the trajectory of movement. The sealing element 7 is preferably embodied as a float for floating on a liquid; in the application in a dialysis fluid circulation: for floating on the dialysis fluid.

If liquid rises from the bottom to the top in the body 6, then the sealing element 7 is completely in contact with the closing element 5, causing it to seal due to its weight in the lower position 4. The liquid and/or gas and/or vapor lifts the sealing element 7, which is designed to float, and thus makes it possible for the gas to escape through the membrane of the hydrophobic filter 1 until the sealing element 7 is pressed against the closing element 2 in position 3 and seals it. Then no further escape of liquid, vapor and/or gas is possible. In the embodiment of the sealing element 7 as a float, a buoyant force acts on the sealing element 7 as a sealing force in the upper position 3.

In this arrangement, it is advantageous that a pressure test performed in a connected fluid circuit does not cause any damage to the hydrophobic membrane.

It is advantageous here that an inexpensive production is made possible.

It is also advantageous in conjunction with the use of the air vent valve for venting a filter in a fluid circulation of a blood treatment machine, in particular in a dialysis machine, that by closing the closing element 5 in the lower position 4, no air can penetrate during operation of the blood treatment due to pressure fluctuations and thus no air can go back to the filter due to pumping.

The sealing element 7 is advantageously made of an elastic plastic, such that the surface is advantageously made of or coated with a hydrophobic material. This achieves the result that the sealing element in position 3 experiences an additional force caused by the surface tension in addition to the buoyant force and thus supports the contact pressure of the sealing element 7 against the receptacle device 2 and thereby supports the imperviousness in position 3.

The weight of the sealing element 7 is advantageously selected so that a sealing force sufficient to form a seal in the lower position 4 is present in the absence of liquid in the body 6 because of the weight force of the sealing element 7.

Figure 1B:
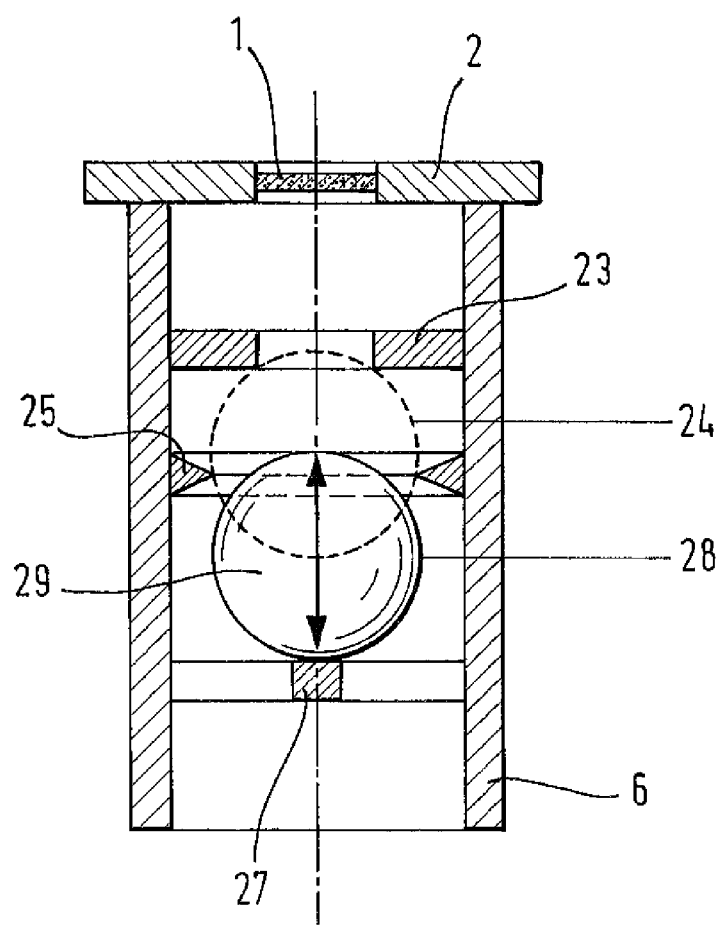
FIG. 1*b* shows another embodiment of the venting valve.

FIG. 1b shows an alternative embodiment of the apparatus described in conjunction with FIG. 1a. The same or corresponding elements are provided with the same reference numerals as in FIG. 1a, and reference is made to the description of FIG. 1a instead of repeating that here. Instead of the sealing element 7, there is a spherical sealing element 29 which can move essentially up and down in a preferably cylindrical cavity in the hollow body 6, moving between a lower position 28, defined by the closing element 27, and an upper position 24, defined by the closing element 2, or in an advantageous refinement, by the limiting element 23 which is additionally provided. The hydrophobic membrane 1, the closing element 2 and the preferably cylindrical body 6 correspond to the elements described in conjunction with FIG. 1a. In addition, the arrangement of FIG. 1b has a closing element 27, which is connected to the preferably cylindrical body 6. The closing elements 2 and 27 may be designed in one piece with the body 6.

A retaining element 25 is arranged between the limiting element 23 and the closing element 27 in such a way that when the sealing element 29 is in position 24, it completely seals the opening in the limiting element 23 and in the retaining element 25 so that it is airtight, vapor-tight and/or fluid-tight and it is additionally held in position 24 by the retaining element 25 but forms a flow passage for gases and liquids in the lower position 28. The retaining element 25 is designed so that the sealing element 29 can be shifted from position 24 to position 28 and/or from position 28 to position 24 only by applying a sufficiently great force. The application of force is advantageously implemented through pressure, which is built up by a pump, for example, in a closed circulation connected to the air vent valve. In venting a filter connected to the air vent valve, air escapes first from the top to the bottom through the body 6, and only when liquid has raised the sealing element 9 floating on the liquid to the extent that it forms an airtight and liquid-tight seal with the sealing element 25 can the required pressure and thus the required force be built up through the supply of additional liquid to move the movable sealing element 29 into position 24. Conversely, by generating a sufficiently high vacuum, the sealing element 29 can be moved from position 24 to position 28 and thus a continuous connection in the body 6 can be established. The movable sealing element 29 and/or the retaining element 25 is/are preferably made of an elastic material, for example, soft plastic, rubber or the like. The required pressure to bring the sealing element 29 into position 24 is advantageously influenced through the choice of material and the dimensions of the sealing element 29, for example, as well as the diameter of the opening provided in the retaining element 25, such that the pressure is greater than the pressure fluctuations which may occur during operation of a fluid circulation connected to the air vent valve, for example, of a dialysate circulation of a blood treatment machine. It is thus possible to prevent inadvertent opening combined with unwanted admission of air. On the other hand, the required pressure should be lower than the maximum pressure that can be created by the connected apparatus. It is thus advantageously possible to achieve the result that the apparatus can be operated automatically by the apparatus without any additional equipment on the front side of the machine when the air vent valve is arranged on the back side of the machine. It is also advantageous that the valve can be opened again and thus when used in a dialysate circulation of a dialysis machine, more rapid emptying with less residue is possible after the treatment and reinfusion.

Figure 1C:
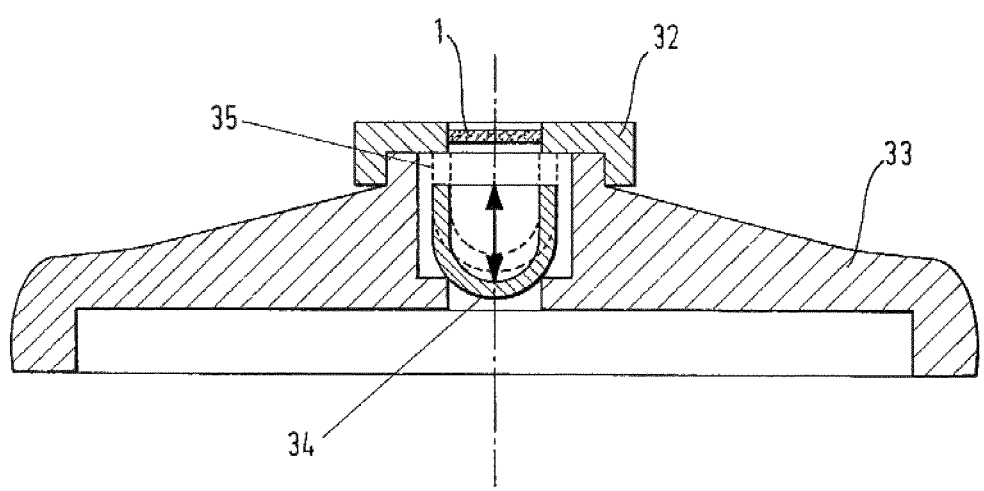
FIG. 1*c* shows the integration of a venting valve into a housing of a filter device.

FIG. 1c shows an advantageous embodiment of an advantageous integration of the apparatus according to FIG. 1a in a variant in which the housing of the filter apparatus is preferably in a cover of the filter housing.

In a manner similar to that with the apparatuses described above, this apparatus of FIG. 1c has a hydrophobic membrane 1, which may be a sterile filter at the same time, a closing element 32 designed as an apparatus to hold the hydrophobic membrane 1, being connected to the base body 33, which is preferably cylindrical on the inside, and at the same time also preferably forms the cover of a filter housing, which is open in both directions, and completely closes the housing at a first end, preferably the upper end. However, the movable sealing element shown in position 34 in FIG. 1c can move from position 34 to position 35 essentially along an axis preferably running vertically along the preferably cylindrical cavity in the base body 33. The two positions are predetermined so that in position 35, the movable part forms an airtight, vapor-tight and/or liquid-tight closure with pressure against the closing element 32 and in position 34 the movable sealing element forms an airtight, vapor-tight and/or liquid-tight closure with pressure against the closing element 32. The force with which the movable sealing element is pressed is obtained in position 35 from the pressure difference between the interior and the exterior as well as the buoyant force of the floating sealing element minus the force of the weight force; in position 34 the contact force is obtained from the weight force and the pressure difference.

The invention claimed is:

1. A filter, for a dialysis liquid circulation, having an air vent valve for venting the filter, the air vent valve comprising a cavity having a first opening and a second opening and a sealing element in the interior of the cavity for sealing the first opening in a first position and for sealing the second opening in a second position, wherein the sealing element is freely movable between the first position and the second position, wherein the second opening is provided with a hydrophobic membrane, wherein the sealing element does not contact the hydrophobic membrane in the movement between the first and second positions, and wherein a flow is formed between the first and second openings when the sealing element is in an intermediate position between the first position and the second position.

2. The filter according to claim 1, wherein during operation of the dialysis fluid circulation, a vertical direction and a horizontal direction are defined, and the sealing element is movable between the first position and the second position during operation of the dialysis fluid circulation with a movement component in the vertical direction.

3. The filter according to claim 1, wherein the sealing element is designed to float on the surface in a liquid.

4. The filter according to claim 3, wherein a surface of the sealing element comprises a hydrophobic material.

5. The filter according to claim 3, wherein the sealing element has a cup shape or the shape of a hemispherical shell or the shape of a ball // sphere.

6. The filter according to claim 5, wherein the sealing element has a guide lip for guiding the sealing element between the first and second positions.

7. The filter according to claim 1, wherein the sealing element is retained in the second position with a seal by a pressure-releasable catch engagement.

8. The filter according to claim 7, wherein the material of the sealing element has elastic properties.

9. The filter according to claim 1, wherein the air vent valve is integrated into a vent cap of the filter.

10. A dialysis fluid circulation for preparing dialysis fluid, having a filter according to claim 1.

* * * * *